United States Patent [19]

Krag et al.

[11] Patent Number: 4,987,892

[45] Date of Patent: Jan. 29, 1991

[54] SPINAL FIXATION DEVICE

[76] Inventors: Martin H. Krag; Malcolm H. Pope, both of Pfizer Inc., 235 E. 42nd St., New York, N.Y. 10017

[21] Appl. No.: 456,085

[22] Filed: Dec. 21, 1989

Related U.S. Application Data

[63] Continuation of Ser. No. 333,855, Apr. 4, 1989, abandoned, and a continuation of Ser. No. 8,693, Jan. 30, 1987, abandoned.

[51] Int. Cl.$^5$ .............................................. A61F 5/04
[52] U.S. Cl. ...................................................... 606/61
[58] Field of Search ........... 128/92 YM, 92 YF, 92 Z, 128/92 Z W, 69

[56] References Cited

U.S. PATENT DOCUMENTS

| | | | |
|---|---|---|---|
| 2,250,417 | 7/1941 | Ettinger | 128/92 Z |
| 2,406,987 | 9/1946 | Anderson | 128/92 ZW |
| 2,497,626 | 2/1950 | Persall | 128/92 Z |
| 4,289,124 | 9/1981 | Zickel | 128/92 YF |
| 4,433,677 | 2/1984 | Ulrich et al. | 128/92 YM |
| 4,445,513 | 5/1984 | Ulrich et al. | 128/92 YM |
| 4,611,580 | 9/1986 | Wu | 128/92 YF |
| 4,648,388 | 3/1987 | Steffee | 128/92 YF |

FOREIGN PATENT DOCUMENTS

| | | |
|---|---|---|
| 2845647 | 2/1987 | Fed. Rep. of Germany . |
| 3132520 | 6/1982 | Fed. Rep. of Germany . |
| 3624067 | 2/1987 | Fed. Rep. of Germany . |
| 3219575 | 2/1988 | Fed. Rep. of Germany . |
| 3504495 | 2/1988 | Fed. Rep. of Germany . |
| 633174 | 11/1982 | Switzerland . |

OTHER PUBLICATIONS

Martin H. Krag, M.D. et al., "An Internal Fixator for Posterior Application to Short Segments of the Thoracic, Lumbar or Lumbosacral Spine, Clinical Orthopaedics and Related Research", No. 203, Feb., 1986, pp. 75-98.

Bulletin Nr. 70, "Neuheiten und Modifikationen im Original—Instrumentarium der Arbeitsgemeinschaft fur Osteosynthesefragen (AO)," 9/1984.

*Primary Examiner*—John D. Yasko
*Attorney, Agent, or Firm*—Peter C. Richardson; Lawrence C. Akers; Elizabeth O. Slade

[57] ABSTRACT

A device for spinal fixation comprises first and second pedicle screw members, a stabilizing member, and an articulating clamp which has securing means for releasably attaching the screw members to the stabilizing member. The device includes locking means such as a clamp bolt to lock the screw members to the articulating clamp.

9 Claims, 2 Drawing Sheets

SPINAL FIXATION DEVICE

This is a continuation of application Ser. No. 07/333,855, filed on Apr. 4, 1989 which is a continuation of Ser. No. 07/008,693 filed Jan. 30, 1987, now abandoned.

BACKGROUND OF THE INVENTION

The present invention relates to a spinal fixation device and a method for fixation of that device between two or more vertebrae. More particularly, it relates to a fixation device that results in inherent structural strength due to a unique method for placement of and linkage between the pedicle screws.

One of the significant problems associated with the design of a spinal fixation device is the need for to localize the involvement of the spinal column. Such a fixation device design should involve fixation directly at the site of instability rather than two or three vertebrae away from it. The fixation device should rely on bony tissue rather than intact soft tissue to achieve stabilization and maximum patient comfort, and to encourage rehabilitation. A spinal fixation device should be fully internalized, with no pins transfixing the skin or muscle. Further, it is important that the device be easy to implant in an accurate and consistent manner.

U.S. Pat. No. 4,604,995 discloses a surgical implant having a unitary rod with a generally rectangular configuration formed by a pair of spaced apart branches which are mirror image duplications of one another and equally spaced along their entire length.

U.S. Pat. No. 4,078,559 discloses a straightening and supporting device for the spinal column. The device comprises a rod shaped supporting member at least the length of the spinal column area to be treated and exerting a straightening and supporting effect on the vertebrae of the spinal column.

U.S. Pat. No. 4,003,376 discloses an apparatus for straightening the spinal column. The apparatus includes an elongated member securable forwardly of and against the spinal column. A pair of fastening devices extend around the spinal column from the elongated member to a pair of bands located rearwardly of and adjacent the spinal column.

SUMMARY OF THE INVENTION

The prosthesis of the present invention overcomes technical, surgical, and practical shortcomings of the prior art. Important features of the present invention are the ability to provide three-dimensional stability adaptibility which allows for safer and more secure implantation of the device.

The device of the present invention combines all of these features in one fixation device. These and other features discussed hereinafter result in a device which is dynamically stable and promotes a smooth and natural movement, while accurately and consistently fixing the spine.

The present invention is directed to a device for spinal fixation comprising a first and second pedicle screw member, a stabilizing member, and an articulating clamp having securing means for releasably attaching the screw members to the stabilizing member, and locking means to lock the screw members to the articulating clamp.

BRIEF DESCRIPTION OF THE DRAWINGS

The novel features and advantages of the present invention will become apparent from a reading of the following detailed description in conjunction with the accompanying drawings wherein.

DESCRIPTION OF THE PREFERRED EMBODIMENT

Figure 2:
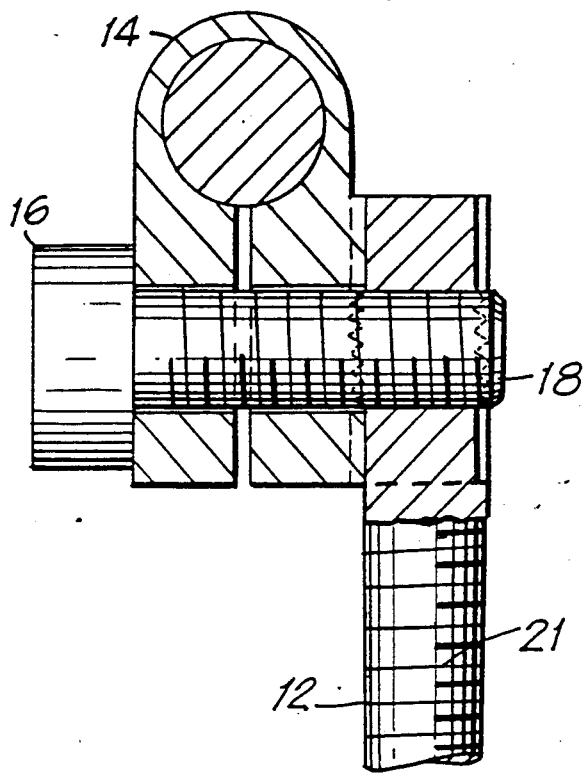
FIG. 2 is a cross-sectional view of the spinal fixation prosthesis of FIG. 1 taken along lines 2—2 of FIG. 1.
Figure 3:
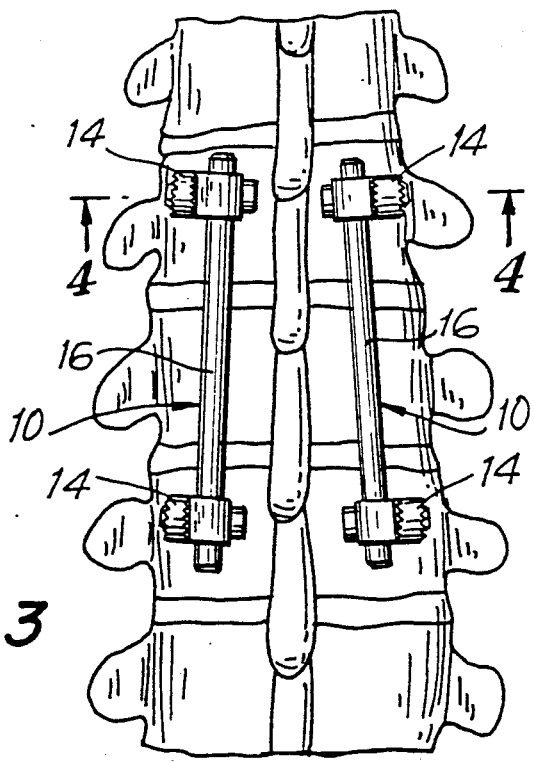
FIG. 3 is a front view of the spinal fixation prosthesis in position in the spinal column.
Figure 4:
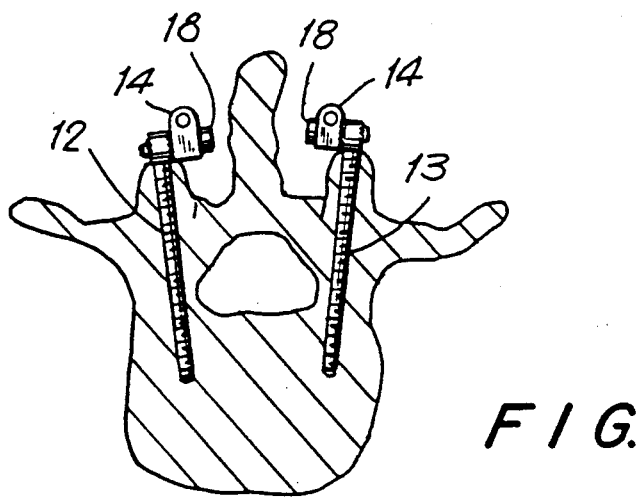
FIG. 4 is a cross-sectional view taken along lines 4—4 of FIG. 3.
Figure 1:
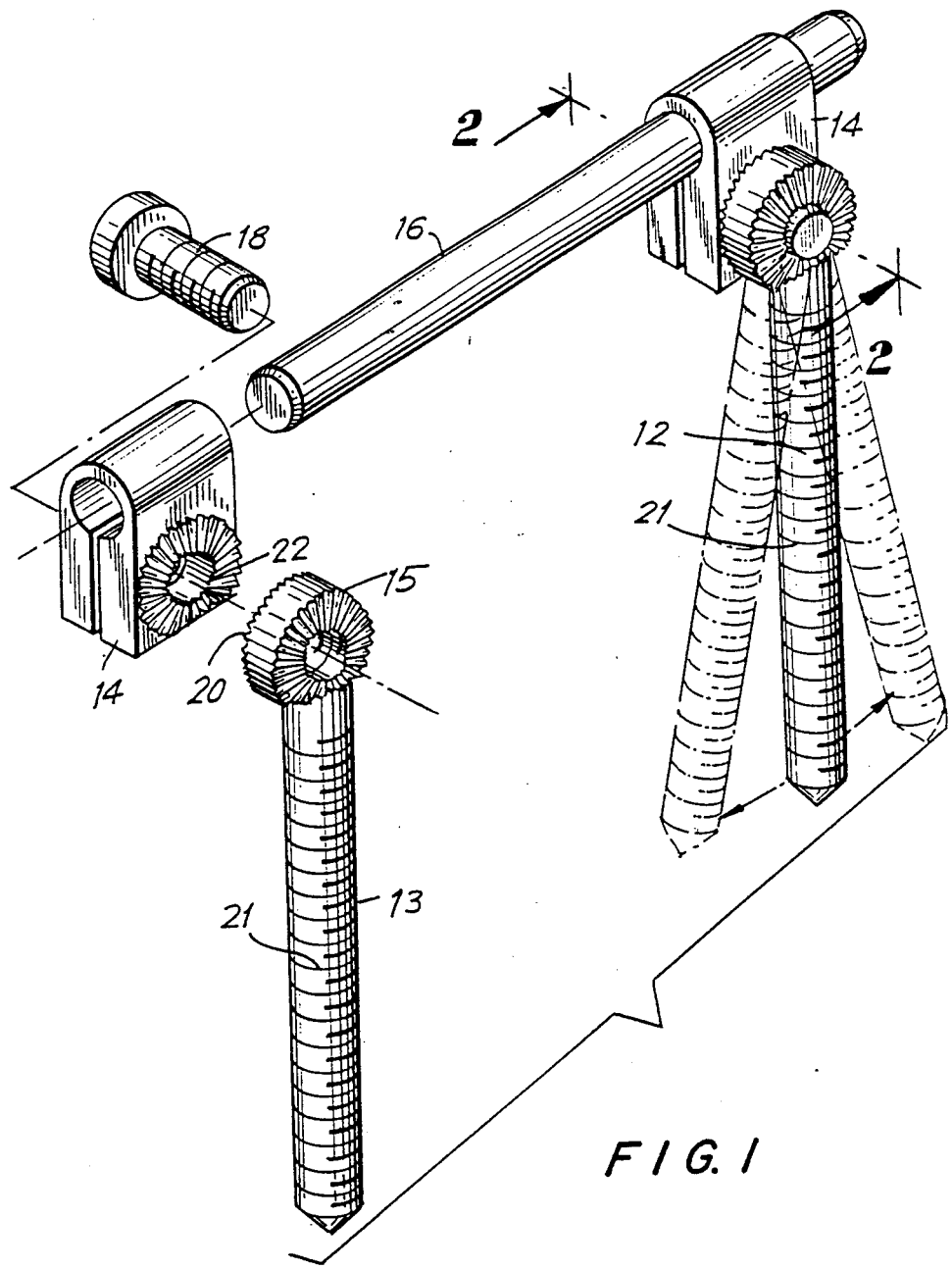
FIG. 1 is an exploded perspective view of a spinal fixation prosthesis of the invention.

In FIGS. 1–4 is illustrated a spinal fixation device for immobilizing two or more vertebrae in the spinal column of a patient. The spinal fixation device generally indicated at 10 includes first and second pedicle screw members 12, 13, respectively, two articulating clamps 14, a stabilizing member 16, and two clamp bolts 18.

The proximal ends 15 of the pedicle screw members 12, 13 are scored with radially arranged teeth 20. Preferably, the screws contain from about 10 to 100 teeth, most preferably 60 to 90 teeth. Each of the articulating clamp 14 includes corresponding teeth 22 for securing the screw members 12, 13 to the articulating clamp 14.

Adjustment of the position of the screw members 12 and 13 relative to stabilizing member 16 is accomplished by (1) rotational motion of teeth 20 on screw members 12 and 13 about teeth 22 on articulating clamps 14, (2) rotational motion of articulating clamps 14 about stabilizing member 16 and (3) sliding motion of articulating clamps 14 along stabilizing member 16.

The screw members 12, 13 are preferably from about 30 mm to 60 mm long, with the diameter of the pedicle screw member being preferably from about 2 mms to 8 mms, and most preferably include a Spiralock TM thread which is primarily used in aircraft and other high vibration applications.

After adjustment, the position between screws 12 and 13 is locked by tightening clamp bolt 18, thus preventing the aforementioned rotational and sliding motions. The threads 21 of the screw members 12, 13 can be tightened and loosened repeatedly without degradation and have an even load distribution along the engaged threads.

The stabilizing member 16 is preferably a rod-shaped member with a diameter of from about 2 mm. to 10 mm. The rod should have a length appropriate for the clinical application.

The threaded clamp bolt 18 preferably has a hexagonal head with a major diameter of from about 2.0 mm. to 8 mm., and an overall length of from about 10 mm. to 20 mms.

Preferably, the stabilizing member, articulating clamps, and first and second pedicle screw members are made from titanium, cobalt chromium surgical implant alloy or, most preferably, 316B strain hardened stainless steel. Additionally, the articulating clamps, stabilizing member and clamp bolts may be made from biocompatible polymeric material.

The components of the spinal fixation device are preferably manufactured by standard machining techniques, for example drilling, burning, grinding, milling and electric polishing.

The use of spinal fixation device 1 will be described with reference to the fixation of the spine at level T12 and into L2.

The patient is anesthetized while lying on his/her back, then turned onto his/her stomach, using an operating table which is radiolucent. The incision is (midline) longitudinal over a vertebrae to be instrumented (for example for an L1 burst fracture). Standard techniques are used for clearing soft tissue off the posterior aspects of the bone out as far as the tips of the transverse processes in a lateral direction. An x ray image intensifier is used to ensure that the proper levels are dissected, and to guide implantation throughout the procedure. The entry site for the first drill hole is tentatively identified, the drill guide is placed over this site and oriented so that by using the image intensifier, the drill guide is centered over the pedicle. The proper sized diameter drill is then used to begin the drill hole, the image intensifier is rotated to show a lateral view, and the drill bit is advanced until the selected depth is obtained, (but not so deep as to penetrate through the anterior cortex). The drill bit is then withdrawn, and a vertebral screw of appropriate length and diameter (chosen ahead of time, usually based on the CT scan x-rays pre-operatively), is then threaded into place. A similar procedure is performed at each of the other three pedicles (four screws are used in most common applications). The articulating mechanism is then loosely attached to each screw head. Next, the longitudinal rod is selected for proper length, so that it just barely protrudes above the upper articulating clamp and below the lower articulating clamp. If movement of the vertebra needs to be produced, it is now done at this time, using a special instrument that grips onto the head of the vertebral screws. While this position is held, the clamp bolts are then tightened using the clamp bolt wrench. At this point, if desired (as is generally the case), a bone graft is then put in place and the incision is closed.

We claim:

1. A device for internalized spinal fixation having three-dimensional adjustability and requiring no violation of the spinal canal, said device comprising:
    (a) a first and a second bone screw adapted to be screwed at least into a first and a second pedicle, respectively, of two vertebrae along one side of a spinal column and for anchoring the device posteriorly with respect to the patient's body in the pedicle area of the spine, said first bone screw to be screwed at least into a pedicle of a first vertebra and said second bone screw to be screwed at least into a pedicle of a second vertebra,
    (b) a rigid stabilizing rod,
    (c) a pair of articulating clamps slidably and rotatably positionable at opposite ends of said stabilizing rod, each of said clamps having a securing means for fixedly but releasably attaching one of said bone screws to the stabilizing rod, but without requiring said bone screws to be parallel to each other, wherein said securing means comprises radially arranged teeth located on the proximal surface of a bone screw and corresponding intermeshable radially arranged teeth located on a surface of an articulating clamp, and
    (d) locking means to lock each bone screw to the articulating clamp to which it is to be attached.

2. A device of claim 1 wherein the locking means is a pair of threaded clamp bolts, each clamp bolt of which locks into threads in an articulating clamp and into threads in one of said bone screws.

3. A device of claim 2 wherein the bone screws are made of stainless steel and are further adapted to be screwed not only into a pedicle but also into the body of a vertebra.

4. A device of claim 3 wherein the bone screws are tapered each at their distal-most portion for ease of insertion.

5. A device of claim 4 wherein the first and second bone screws each has self-tapping threads at its distal-most portion.

6. A surgical method for spinal fixation comprising the steps of:
    (a) making an incision of appropriate length and orientation in the back of a patient,
    (b) exposing the posterior surface of the vertebrae in the region where fixation of two different vertebrae is desired,
    (c) drilling pilot holes in two pedicles located in said two different vertebrae but on the same side of the spinal column,
    (d) inserting a bone screw into each pilot hole so that each bone screw is inserted at least into a pedicle, wherein it is not required that the two bone screws are parallel,
    (e) assembling a pair of articulating clamps at opposite ends of a rigid stabilizing rod, wherein said pair of articulating clamps are slidably and rotatably positionable at opposite ends of said stabilizing rod, wherein each of said clamps has a securing means for fixedly but releasably attaching one of said bone screws to said stabilizing rod, wherein said securing means comprises radially arranged teeth located on the proximal surface of a bone screw and corresponding intermeshable radially arranged teeth located on a surface of an articulating clamp, and then connecting each of said bone screws with an articulating clamp,
    (f) properly positioning the vertebrae,
    (g) locking each bone screw to an articulating clamp, and
    (h) closing the surgical site.

7. A device according to claim 1, wherein said rigid stabilizing rod has a length which is adapted to span about at most only three vertebrae.

8. A device according to claim 1, wherein said rigid stabilizing rod has a length which is adapted to span about at most only two vertebrae.

9. A combination comprising a device according to claim 1 to be placed onto a first side of the spinal column and another device according to claim 1 to be placed on to a second side of the spinal column.

* * * * *